United States Patent
Zhou et al.

(10) Patent No.: US 12,290,589 B2
(45) Date of Patent: May 6, 2025

(54) COSMETIC AND PERSONAL CARE COMPOSITIONS CONTAINING CATIONIC SURFACTANTS AND ANIONIC COMPOUNDS

(71) Applicant: L'OREAL, Paris (FR)

(72) Inventors: XianZhi Zhou, Millburn, NJ (US); Siliu Tan, Westfield, NJ (US)

(73) Assignee: L'OREAL, Paris (FR)

( * ) Notice: Subject to any disclaimer, the term of this patent is extended or adjusted under 35 U.S.C. 154(b) by 532 days.

(21) Appl. No.: 17/136,893

(22) Filed: Dec. 29, 2020

(65) Prior Publication Data

US 2022/0202686 A1    Jun. 30, 2022

(51) Int. Cl.
| | | |
|---|---|---|
| A61K 8/81 | (2006.01) | |
| A61K 8/04 | (2006.01) | |
| A61K 8/34 | (2006.01) | |
| A61K 8/41 | (2006.01) | |
| A61K 8/49 | (2006.01) | |
| A61K 8/898 | (2006.01) | |
| A61Q 5/12 | (2006.01) | |

(52) U.S. Cl.
CPC .............. *A61K 8/8147* (2013.01); *A61K 8/04* (2013.01); *A61K 8/342* (2013.01); *A61K 8/416* (2013.01); *A61K 8/4973* (2013.01); *A61K 8/817* (2013.01); *A61K 8/898* (2013.01); *A61Q 5/12* (2013.01); *A61K 2800/10* (2013.01); *A61K 2800/5424* (2013.01); *A61K 2800/594* (2013.01); *A61K 2800/596* (2013.01)

(58) Field of Classification Search
CPC ........ A61K 8/8147; A61K 8/04; A61K 8/342; A61K 8/416; A61K 8/4973; A61K 8/817; A61K 8/898; A61K 2800/10; A61K 2800/5424; A61K 2800/594; A61K 2800/596; A61K 8/922; A61Q 5/12
See application file for complete search history.

(56) References Cited

U.S. PATENT DOCUMENTS

| | | |
|---|---|---|
| 5,928,657 A | 7/1999 | Simon |
| 6,024,947 A | 2/2000 | Gagnebien et al. |
| 8,668,746 B2 | 3/2014 | Uellner |
| 10,058,494 B2 | 8/2018 | Dreher et al. |
| 10,751,271 B2 | 8/2020 | Murata et al. |
| 2002/0037267 A1 | 3/2002 | Guillou et al. |
| 2006/0078520 A1 | 4/2006 | Pays et al. |
| 2011/0240050 A1 | 10/2011 | Perruna et al. |
| 2012/0251476 A1 | 10/2012 | Molenda et al. |
| 2013/0251648 A1 | 9/2013 | Tong et al. |
| 2014/0105845 A1 | 4/2014 | Bui et al. |
| 2014/0352711 A1 | 12/2014 | Hoffmann et al. |
| 2016/0361246 A1 | 12/2016 | Hoffmann et al. |
| 2017/0209355 A1 | 7/2017 | Tezuka et al. |
| 2018/0098923 A1 | 4/2018 | Hutton, III |
| 2018/0280267 A1* | 10/2018 | Rughani ................ A61K 8/362 |
| 2018/0280270 A1 | 10/2018 | Rughani et al. |
| 2018/0338900 A1* | 11/2018 | Patterson ................ A45D 7/04 |
| 2019/0029948 A1* | 1/2019 | Akerele ................ A61K 8/731 |
| 2021/0369579 A1 | 12/2021 | Liang et al. |

FOREIGN PATENT DOCUMENTS

| | | |
|---|---|---|
| DE | 10307115 A1 | 9/2004 |
| EP | 2797573 B1 | 8/2018 |
| FR | 2852238 A1 | 9/2004 |
| JP | 2007084482 A | 4/2007 |
| WO | 9423696 A1 | 10/1994 |
| WO | 18228898 A1 | 12/2018 |
| WO | 18228899 A1 | 12/2018 |
| WO | 18228900 A1 | 12/2018 |
| WO | 20116480 A1 | 6/2020 |

OTHER PUBLICATIONS

Zakharova et al. International Journal of Molecular Sciences 20.22 (2019): 5534. (Year: 2019).*
Dias et al. International journal of trichology 6.3 (2014): 95. (Year: 2014).*
Mixer Direct. How does liquid viscosity work? 2018. <https://blog.mixerdirect.com/how-liquid-viscosity-works>. Downloaded Oct. 26, 2023. (Year: 2018).*
Fujii et al. International Journal of Cosmetic Science, 2017, 39, 556-563. (Year: 2017).*
Thickening Conditioner, Farmona Laboratorium Kosmetyków Naturalnych, Mintel Record ID No. 5722111, electronically retrieved on Dec. 28, 2020.
Search Report, French Patent Application No. 2106113, mailing date Feb. 17, 2022.
Database GNPD [Online], Mintel, Ethical Living, UK, "Strengthening Conditioner", Record ID 7573015.
Database GNPD [Online], Mintel, Ethical Living, UK, "Volumising Conditioner", Record ID 7573021.
Database GNPD [Online], Mintel, Ethical Living, UK, "Revolutionary Conditioner", Record ID 7537303.
Database GNPD [Online], Mintel, Ethical Living, UK, "Miracle Conditioner", Record ID 7537309.
Database GNPD [Online], Mintel, My Hair Doctor, "Colour Protection Conditioner", Record ID 5467241.
Database GNPD [Online], Mintel, Windle & Moodie, UK, "Ultra Nourishing Conditioner", Record ID 5063085.

(Continued)

*Primary Examiner* — Mina Haghighatian
*Assistant Examiner* — Janice Y Silverman
(74) *Attorney, Agent, or Firm* — POLSINELLI PC

(57) ABSTRACT

The instant disclosure relates to cosmetic compositions that include a non-hydrophobically modified anionic polymer; a cationic surfactant, including a cationizable surfactant; a fatty alcohol; and a cosmetically acceptable solvent; wherein the pH of the composition is below 5. Methods for using such cosmetic compositions are also provided.

20 Claims, 4 Drawing Sheets

(56) References Cited

OTHER PUBLICATIONS

Database GNPD [Online], Mintel, Laperle Haircare, Sweden, "Maria Nila Colour Colour Caring Conditioner", Record ID 2019982.
Search Report, French Patent Application No. FR 2103536, mailing date Jan. 21, 2022.

\* cited by examiner

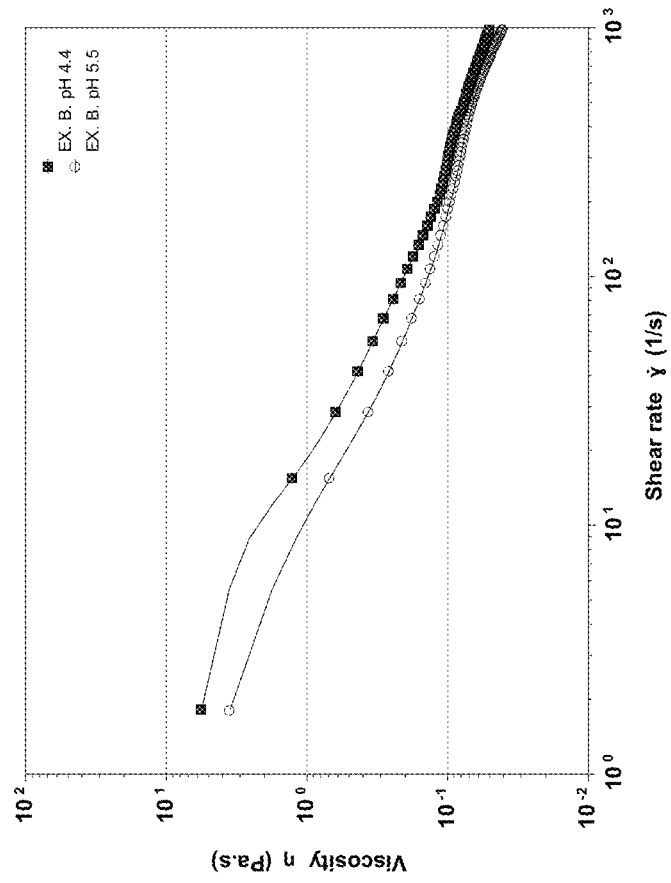
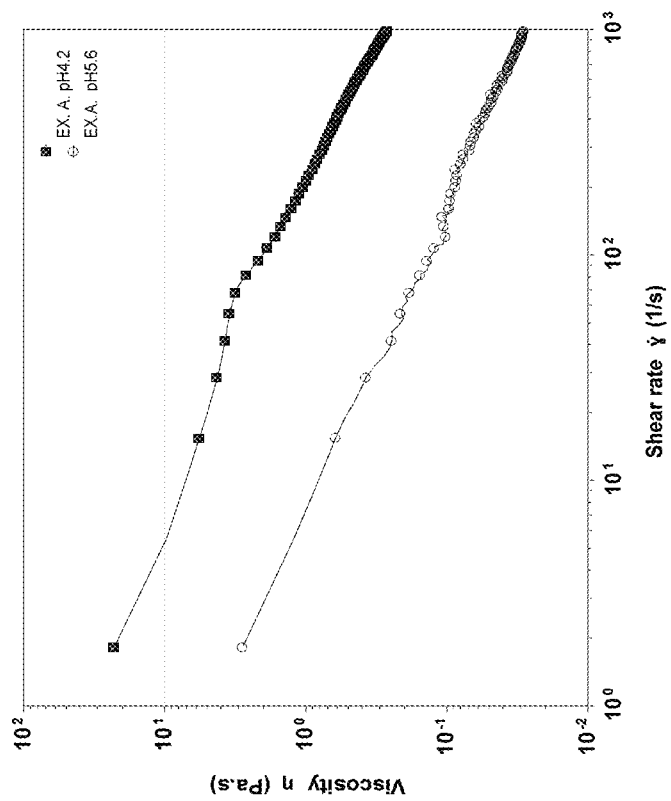
FIG. 1A  FIG. 1B
FIGURE 1

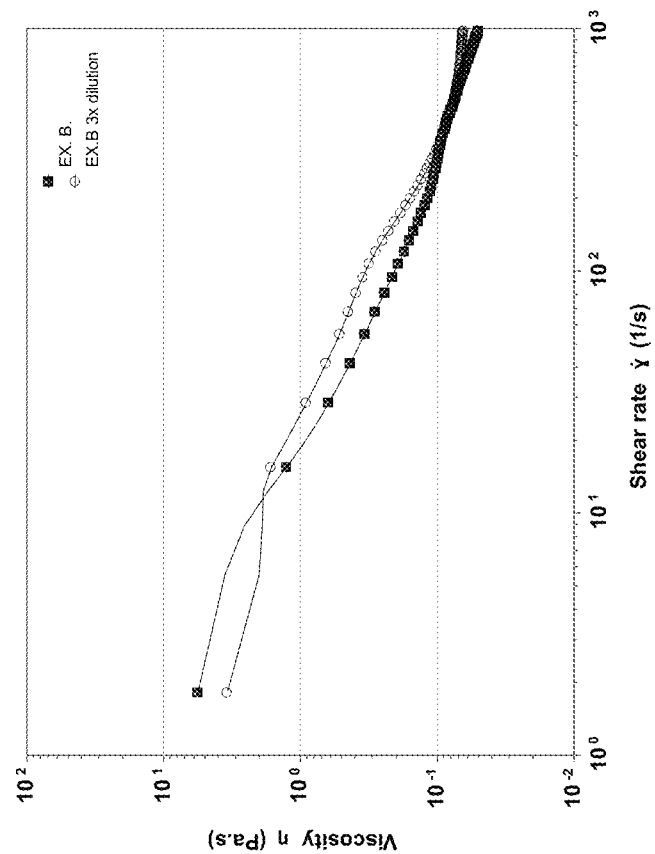
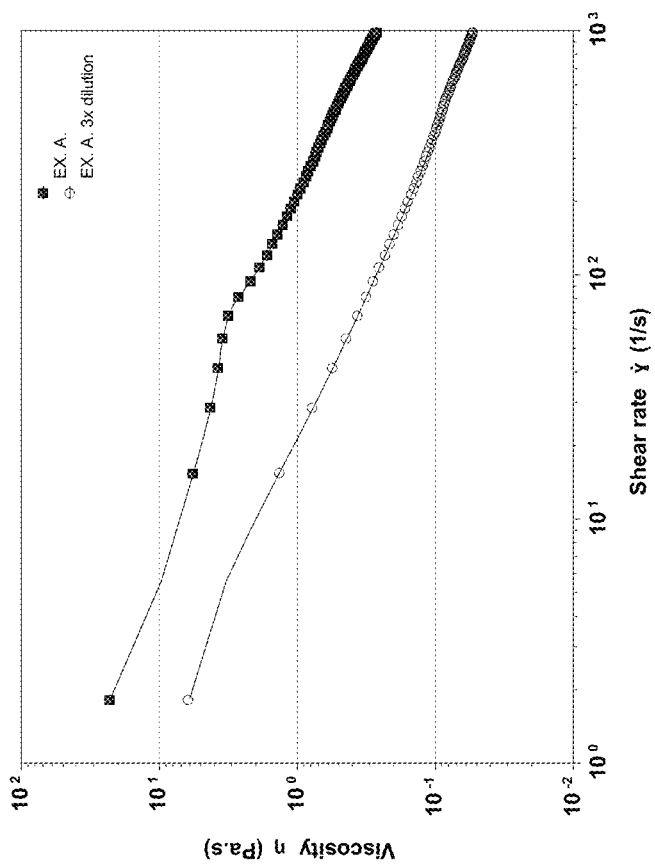
FIG. 2A  FIG. 2B
FIGURE 2

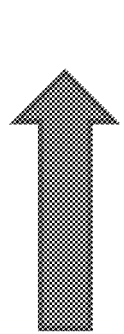
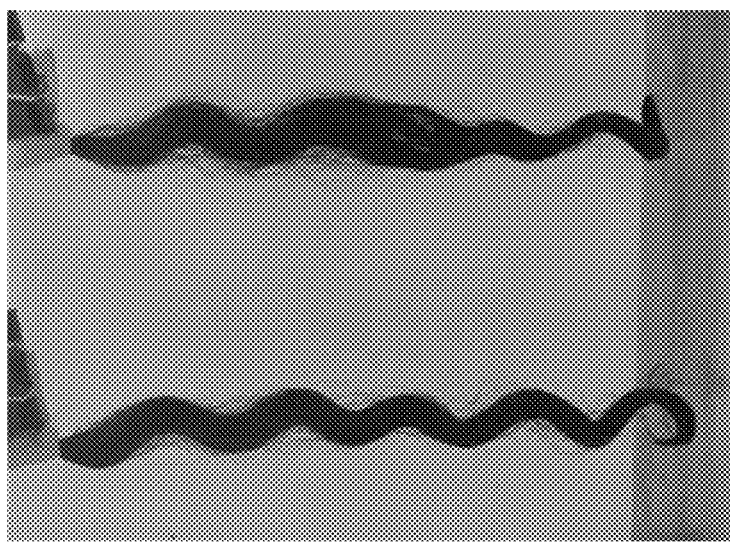
FIG. 3B
25°C, 80%, 2 days
FIG. 3A
FIGURE 3

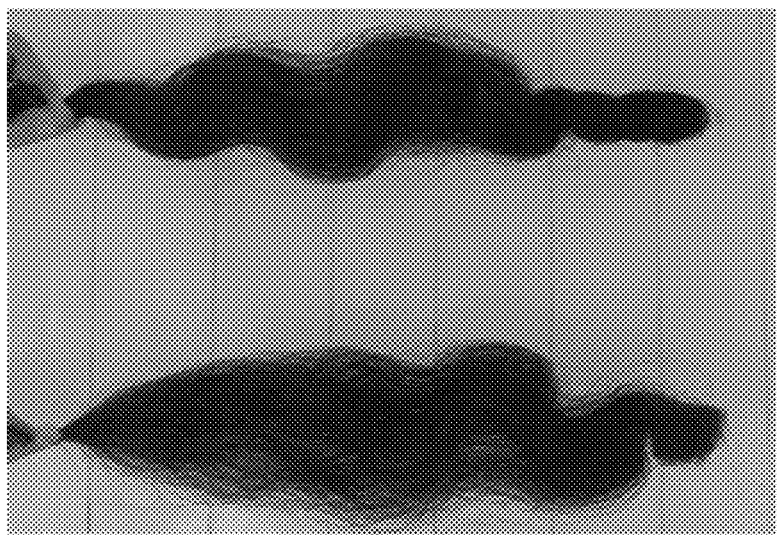
FIG. 4B
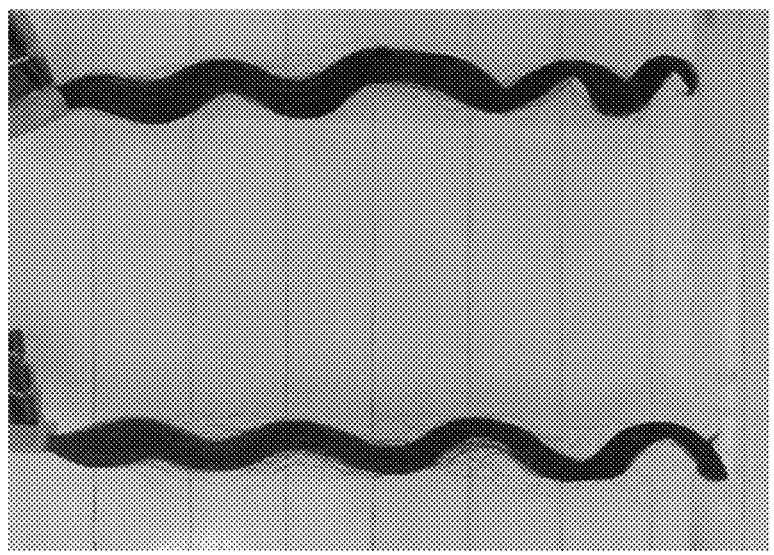
FIG. 4A
FIGURE 4

COSMETIC AND PERSONAL CARE COMPOSITIONS CONTAINING CATIONIC SURFACTANTS AND ANIONIC COMPOUNDS

FIELD OF THE DISCLOSURE

The instant disclosure relates to cosmetic and personal care compositions containing cationic surfactants, anionic compounds selected from anionic polymers, and fatty compounds. The compositions are particularly useful for imparting conditioning or moisturizing properties to keratinous substrates such as hair or skin and have improved rinsability properties. Also disclosed are methods for using the cosmetic compositions.

BACKGROUND

Many consumers desire to use cosmetic and personal care compositions that provide caring and conditioning/moisturizing properties to keratinous substrates such as hair and skin. For example, consumers continuously seek for skin and scalp care products that can provide improved conditioning and moisturizing benefits. They also seek hair care or a hair cosmetic composition products to care for hair that has been subject to chemical treatments such as oxidative hair dyes, hair relaxers, or permanent waving treatments. Many of the chemical treatments as alkaline in nature and may leave residual alkalinity on the treated hair.

While dyeing or color lifting compositions can effectively alter the color of hair, and relaxing, straightening, perming, and waving compositions can effectively alter the shape of the hair, these chemical treatments can damage the hair fibers and/or irritate the scalp. In addition, external factors such as high humidity which causes the hair to become very frizzy, unmanageable, and lose its shape and style or such as mechanical or physical or other external stresses such as brushing, combing, and tangling, and heat can also damage or negatively impact the feel and look of the hair.

Thus, in order to reduce or avoid damage to hair, as well as to improve the cosmetic performance of the compositions, different types of hair products have been developed by manufacturers that are aimed to help consumers improve the quality of hair, feel of the hair, and the manageability of hair as well as reduce or remove the frizziness of hair and condition/moisturize hair, particularly when the hair is damaged. These products are typically provided in forms that are applied as shampoos, conditioners, or treatment such as after or pre-shampooing treatments, and after or pre-conditioning treatments which can be leave-in or rinse-off products.

In addition, consumers desire hair and skin care products, in particular, rinse-off cleansing and rinse-off conditioning products that can be quickly or efficiently removed without leaving noticeable residues and at the same time, deposit conditioning, moisturizing or other cosmetic benefits such as improved hair feel or skin feel properties.

Thus, the object of this invention is related to a composition and method of treating keratinous substrates such as hair or skin wherein the composition will deliver both caring and rinsability/removability properties.

The object of the invention is also to provide a composition and method of treating hair that has been chemically treated or damaged such as hair that has been contacted with a basic or alkaline treatment.

SUMMARY OF THE DISCLOSURE

It has surprisingly been found that compositions and methods of treating keratinous substrates such as hair or skin according to the present invention provide conditioning and moisturizing benefits to the keratinous substrate, as well as other desirable properties such as fast and efficacious rinsability or removability attributes.

One aspect of the invention pertains to a cosmetic composition containing:
(a) at least 0.3 wt. %, based on the total weight of the composition, of at least one non-hydrophobically modified anionic polymer;
(b) at least one cationic surfactant, including a cationizable surfactant;
(c) at least one fatty alcohol; and
(d) at least one cosmetically acceptable solvent;
wherein the pH of the composition is below about 5.

Another aspect of the invention pertains to methods of treating keratinous substrates such hair or skin, for example, conditioning or moisturizing hair or skin. In some embodiments, the method comprises applying any of the compositions described herein to keratinous substrates. In one or more embodiments, the composition is applied to hair, including curly hair, as part of a hair caring routine. In some embodiments, the composition is applied after treating the hair with a shampoo. In some embodiments, the composition is a rinse-off product. In some embodiments, the rinse-off composition is used as a post-treatment product, following the chemical treatment of hair or treatment of hair with an alkaline product. Such a product can deliver conditioning, moisturizing and repair benefits to the chemically treated hair. In some embodiments, the composition is used as a rinse-off skin care product that can cleanse and at the same time. deliver conditioning and moisturizing benefits.

BRIEF DESCRIPTION OF THE DRAWING

Implementation of the present technology will now be described, by way of example only, with reference to the attached figure, wherein:

FIG. 1 includes graphs showing that the viscosity of the inventive composition significantly changes while the viscosity of a comparative composition does not significantly change when the pH of each composition is increased.

FIG. 2 includes graphs showing that the viscosity of the inventive composition significantly changes while the viscosity of a comparative composition does not significantly change when each composition undergoes a 3× dilution with water FIG. 3 includes photographs of hair swatches treated with the inventive and the comparative composition right after treatment (initial) and after two days in a humidity chamber at 80% relative humidity.

FIG. 4 includes photographs of hair swatches treated with the comparative and the inventive composition the right after treatment (initial) and after two days of air drying.

It should be understood that the various aspects are not limited to the arrangements and instrumentality shown in the drawings.

DETAILED DESCRIPTION OF THE DISCLOSURE

The term "cosmetic composition" encompasses many types of compositions for application to keratinous substrates such as hair or skin. When the substrate is hair, the compositions can take be hair lotions, hair emulsion creams, hair conditioners, hair masques (masks), etc., which can be used either as leave-on or rinse-off treatments or products. A cosmetic composition such as a hair cosmetic composition according to the invention is characterized by its ability to provide a cosmetic (such as caring) benefit to the substrate. Non-limiting examples of benefits that can be imparted by the compositions of the present invention to hair include one or more of frizz control, curl definition, discipline, volume control, manageability, smoothness, sleekness, softness, suppleness, hydration or moisture (does not feel dry) and natural feel. At the same time, even when the compositions of the present disclosure contain fatty compounds such as fatty alcohols, silicones, and plant- or vegetable-based oils, surprisingly, a light weight feel and a clean feel (non-greasy, non-oily) are imparted to the hair.

The cosmetic compositions of the instant disclosure typically include:
(a) at least 0.3 wt. %, based on the total weight of the composition, of at least one non-hydrophobically modified anionic polymer;
(b) at least one cationic surfactant, including a cationizable surfactant;
(c) at least one fatty alcohol; and
(d) at least one cosmetically acceptable solvent;
wherein the pH of the composition is below about 5.

In an embodiment, the cosmetic composition has a lamellar gel network.

In an embodiment, the at least one non-hydrophobically modified anionic polymer is a copolymer of two or more monomers selected from the group consisting of acrylic acid, methacrylic acid, and their simple esters chosen from methyl, ethyl esters and ethylhexyl esters.

In an embodiment, when the at least one non-hydrophobically modified anionic polymer comprises an alkyl group, the alkyl group is less than 5 carbons.

In an embodiment, the at least one non-hydrophobically modified anionic polymer is not neutralized or partially neutralized.

In an embodiment, the at least one non-hydrophobically modified anionic polymer is an aqueous dispersion.

In an embodiment, the at least one non-hydrophobically modified anionic polymer is a latex polymer.

In an embodiment, the at least one non-hydrophobically modified anionic polymer is acrylates copolymer.

In an embodiment, the at least one non-hydrophobically modified anionic polymer is present in an amount of from about 0.3 to about 5 wt. %, or about 0.5 to about 4 wt. %, or about 0.6 to about 4 wt. %, or about 0.6 to about 3 wt. %, or about 0.7 to about 2.5 wt. %, based on the total weight of the cosmetic composition, including ranges and sub-ranges there between.

In an embodiment, the at least one cationic surfactant is selected from:
quaternary ammonium salts corresponding to the general formula below:

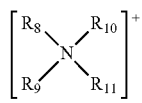

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms;

a quaternary ammonium salt of imidazoline;
a quaternary diammonium or triammonium salt, in particular of formula:

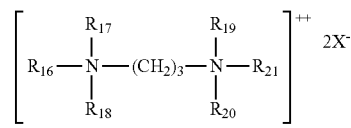

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N—(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates; and cationizable surfactants, including cationizable surfactants together with an acid neutralizer selected from compounds of the general structure $R_4$-A-$R_5$—B,
wherein $R_4$ is a saturated or unsaturated, straight or branched alkyl chain with 8 to 24 C atoms, $R_5$ is a straight or branched alkyl chain with 1 to 4 C atoms, A is selected from:

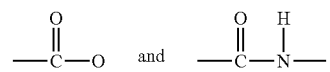

and B is selected from

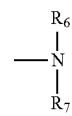

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

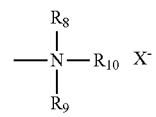

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms, or mixtures thereof.

In an embodiment, the at least one cationic surfactant is selected from quaternary diammonium or triammonium salts, in particular of formula:

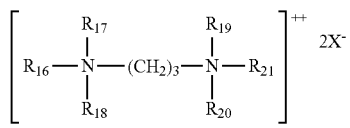

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates.

In an embodiment, the at least one cationic surfactant is selected from cationizable surfactants, including cationizable surfactants together with an acid neutralizer selected from compounds of the general structure $R_4$-A-$R_5$—B, wherein $R_4$ is a saturated or unsaturated, straight or branched alkyl chain with 8 to 24 C atoms, $R_5$ is a straight or branched alkyl chain with 1 to 4 C atoms, A is selected from:

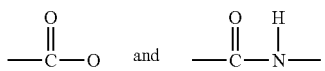

and B is selected from

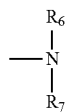

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

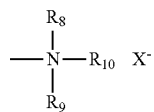

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In an embodiment, the at least one cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In an embodiment, the at least one cationic surfactant includes behentrimonium chloride.

In an embodiment, the at least one cationic surfactant includes cetrimonium chloride.

In an embodiment, the at least one cationic surfactant is chosen from behentrimonium chloride, cetrimonium chloride, or a mixture thereof.

In an embodiment, the at least one cationic surfactant is selected from oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In an embodiment, the at least one cationic surfactant includes stearamidopropyl dimethylamine.

In an embodiment, the at least one cationic surfactant the at least one cationic surfactant is present in an amount of from about 0.1 to about 5 wt. %, or about 0.1 to about 4 wt. %, or about 0.2 to about 4 wt. %, or about 0.3 to about 3 wt. %, or about 0.5 to about 2.5 wt. %, based on the total weight of the cosmetic composition, including ranges and subranges there between.

In an embodiment, the at least one fatty alcohol is selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

In an embodiment, the at least one fatty alcohol is present in an amount of from about 0.5 to about 10 wt. %, or from about 1 to about 8 wt. %, or from about 1.5 to about 6 wt. %, or from about 2 to about 7 wt. %, based on the total weight of the cosmetic composition, including ranges and sub-ranges there between.

In an embodiment, the composition of the present invention further comprises at least one amino functionalized silicone selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof.

In an embodiment, the at least one cosmetically acceptable solvent is selected from water, organic solvents, and mixtures thereof.

In an embodiment, the cosmetic composition has pH a ranging from about 2.5 to about 4.8 or from about 2.7 to about 4.5 or from about 3 to about 4.5, including ranges and sub-ranges there between.

In an embodiment, the at least one amino functionalized silicone is present in an amount of about 0.1 to about 5 wt. %, or preferably about 0.3 to about 4 wt. %, or more preferably, about 0.4 to about 3 wt. %, or about 0.5 to about 2 wt. %, based on the total weight of the cosmetic composition, including ranges and sub-ranges there between.

In an embodiment, the composition of the present invention further comprises at least one fatty compound selected from at least one plant-based fatty compound including plant-based oils (such as plant-based butters, plant-based triglycerides), hydrocarbon oils, esters, or a mixture thereof.

In an embodiment, the at least one fatty compound is present in an amount of about 0.1 to about 10 wt %, about 0.1 to about 9 wt. %, or about 0.2 to about 8 wt. %, or about 0.3 to about 7 wt. %, or about 0.4 to about 7 wt. %, or about 0.4 to about 6.5 wt. %, or about 0.5 to about 6 wt. %, or 0.5 to about 5 wt. %, or about 0.5 to about 4.5 wt. %, or preferably, about 1 to about 4 wt. %, or more preferably, about 1 to about 3 wt. %, or even more preferably, about 1.5 to about 2.5 wt %, based on the total weight of the cosmetic composition, including ranges and sub-ranges there between.

In an embodiment, the least one fatty compound includes at least one ester selected from fatty esters, cetyl esters, isopropyl esters, glyceryl (glycerol) esters, dialkyl esters, diesters with octanoic acid and propylene glycol (for example, mixture of the propylene glycol diesters of caprylic and capric acids, propylene glycol dicaprylate/ dicaprate, or mixtures thereof, preferably, from cetyl esters, isopropyl esters, glyceryl esters, or mixtures thereof.

In an embodiment, the at least one ester is present in an amount of about 0.01 to about 6 wt %, such as about 0.05 to about 5 wt. %, about 0.05 to about 4.5 wt. %, or such as about 0.1 to about 4 wt. %, based on the total weight of the cosmetic composition, including ranges and sub-ranges there between.

In an embodiment, the total amount of the at least one fatty alcohol(s) is greater than the total amount of the at least one fatty compound in the compositions of the present invention, and ranges from about 10:1 to about 1.5:1, including ranges and sub-ranges there between. In an embodiment, the weight ratio of the at least one fatty alcohol(s) is greater than the total amount of the at least one fatty compound is at about 9:1, 8:1, 7:1, 6:1, 5.7:1, 5.5:1, 5:1, 4:1, 3:1, 2:1, or 1.5:1.

In an embodiment, the composition of the present invention further comprises at least one nonionic surfactant selected from alkoxylated fatty alcohols, alkylpolyglucosides, polysorbates, or mixtures thereof.

The cosmetically acceptable solvent is selected from water, organic solvents, or a mixture thereof.

In an embodiment, the cosmetically acceptable solvent comprises water.

In an embodiment, the cosmetically acceptable solvent comprises water and at least one organic solvent.

In an embodiment, the cosmetic composition of the present invention typically includes:
(a) from about 0.5 to about 4 wt. %, or about 0.6 to about 4 wt. %, or about 0.6 to about 3 wt. %, or about 0.7 to about 2.5 wt. %, of at least one non-hydrophobically modified anionic polymer including acrylates copolymer;
(b) from about 0.2 to about 4 wt. %, or about 0.3 to about 3 wt. %, or about 0.5 to about 3 wt. %, of at least one cationic surfactant, including a cationizable surfactant;
(c) from about 2 to about 7 wt. %, or from about 3 to about 7 wt. %, or about 4 to about 7 wt. % of at least one fatty alcohol selected;
(d) at least one cosmetically acceptable solvent;
(e) optionally, from about 0.1 to about 2 wt. % of at least one silicone;
(f) optionally, from about 0.05 to about 2 wt. % of at least one nonionic surfactant;
(g) optionally, from about 0.1 to about 5 wt. % of at least one fatty compound selected from plant-based oils, hydrocarbon oils, esters, fatty acids, or a mixture thereof; and
wherein the pH of the composition ranges from about 3 to about 4.5;
all weights being based on the total weight of the cosmetic composition.

In an embodiment, the cosmetic composition of the present invention typically includes:
(a) from about 0.7 to about 0.9 wt. % of at least one non-hydrophobically modified anionic polymer including acrylates copolymer;
(b) from about 0.5 to about 2.5 wt. % of at least one cationic surfactant, including a cationizable surfactant and selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, or mixtures thereof;
(c) from about 4 to about 7 wt. % of at least one fatty alcohol selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), decyl alcohol, undecyl alcohol, and a mixture thereof;
(d) at least one cosmetically acceptable solvent;
(e) optionally, from about 0.1 to about 2 wt. % of at least one silicone selected from amino functionalized silicones;
(f) optionally, from about 0.05 to about 2 wt. % of at least one nonionic surfactant;
(g) optionally, from about 0.1 to about 5 wt. % of at least one fatty compound selected from plant-based oils, hydrocarbon oils, esters, fatty acids, or a mixture thereof; and
wherein the pH of the composition ranges from about 3 to about 4.5;
all weights being based on the total weight of the cosmetic composition.

In an embodiment, the present disclosure is directed to treating or contacting a keratinous substrate such as hair or skin with any one of the above described cosmetic compositions.

In an embodiment, the keratinous substrate to be treated with any one of the described cosmetic compositions is hair.

In an embodiment, the present disclosure is directed to a method comprising applying onto hair, any one of the above-described cosmetic compositions wherein the method imparts to hair, one or more of:
- conditioning benefits;
- hair repair benefits;
- frizz control;
- manageability;
- curl definition;
- sleek look;
- smoothness; or
- softness.

In an embodiment, the above-described method comprises or includes a step of alkalizing hair or forming pre-alkalized hair before applying the cosmetic composition onto the hair.

In an embodiment, the present invention is further directed to a fast wash or a fast rinse method, the method comprising:
(1) applying onto a keratinous substrate such as hair or skin, a cosmetic composition comprising:
  (a) from about 0.5 to about 4 wt. %, or about 0.6 to about 4 wt. %, or about 0.6 to about 3 wt. %, or about 0.7 to about 2.5 wt. %, of at least one non-hydrophobically modified anionic polymer including acrylates copolymer;
  (b) from about 0.2 to about 4 wt. %, or about 0.3 to about 3 wt. %, or about 0.5 to about 3 wt. %, of at least one cationic surfactant, including a cationizable surfactant;
  (c) from about 2 to about 7 wt. %, or from about 3 to about 7 wt. %, or about 4 to about 7 wt. % of at least one fatty alcohol selected;
  (d) at least one cosmetically acceptable solvent;
  (e) optionally, at least one silicone;
  (f) optionally, at least one nonionic surfactant;
  (g) optionally, at least one fatty compound selected from non-silicone oils, esters, fatty acids, or a mixture thereof; and
wherein the pH of the composition is below about 5.

In an embodiment, the method further comprises a step of rinsing the keratinous substrate with extraneous water.

Thus, in an embodiment, the present invention is further directed to a fast wash or a fast rinse method, the method being a method of improving the rinsability of a composition from keratinous substrates such as hair of skin and comprising combining:
(a) from about 0.5 to about 4 wt. %, or about 0.6 to about 4 wt. %, or about 0.6 to about 3 wt. %, or about 0.7 to about 2.5 wt. %, of at least one non-hydrophobically modified anionic polymer including acrylates copolymer;
(b) from about 0.2 to about 4 wt. %, or about 0.3 to about 3 wt. %, or about 0.5 to about 3 wt. %, of at least one cationic surfactant, including a cationizable surfactant;
(c) from about 2 to about 7 wt. %, or from about 3 to about 7 wt. %, or about 4 to about 7 wt. % of at least one fatty alcohol selected;
(d) at least one cosmetically acceptable solvent;
(e) optionally, from about 0.1 to about 2 wt. % of at least one silicone;
(f) optionally, from about 0.05 to about 2 wt. % of at least one nonionic surfactant;
(g) optionally, from about 0.1 to about 5 wt. % of at least one fatty compound selected from plant-based oils, hydrocarbon oils, esters, fatty acids, or a mixture thereof; and
wherein the pH of the composition ranges from about 2.5 to about 4.8;
(h) all weights being based on the total weight of the hair cosmetic composition.

When the cosmetic composition is contacted with extraneous water, the viscosity of the composition decreases which allows for improved spreadability and ease of application of the composition on skin or hair.

In various embodiments, when the cosmetic composition of the present disclosure is to be applied onto hair, any one of the above-described methods includes applying the cosmetic composition onto hair that has been previously contacted or pre-treated with an alkaline or basic product or composition, including an oxidative hair dyeing composition or a hair relaxing/straightening composition.

It has also been surprisingly discovered that the combination of the least one non-hydrophobically modified anionic polymer and of the at least one cationic surfactant in a composition for treating hair or, resulted in a faster and improved ease of rinsability of the composition when the pH of the composition is increased, such as when the composition is put in contact with an alkaline or basic composition or substrate or when the composition is applied onto pre-alkalized hair. When the pH of the composition increases, the viscosity of the composition significantly decreases. With a faster and improved ease of rinsability, the rinsing step uses less water.

Thus, in an embodiment, the present invention is further directed to a fast wash or a fast rinse method, the method comprising applying onto pre-alkalized hair or hair having a basic or alkaline pH, a cosmetic composition comprising:
  (a) from about 0.3 wt. %, based on the total weight of the composition, of at least one non-hydrophobically modified anionic polymer;
  (b) at least one cationic surfactant, including a cationizable surfactant;
  (c) at least one fatty alcohol;
  (d) at least one cosmetically acceptable solvent;
  (e) optionally, at least one silicone;
  (f) optionally, at least one nonionic surfactant; and
  (g) optionally, at least one fatty compound selected from non-silicone oils, esters, fatty acids, or a mixture thereof; and
wherein the pH of the composition is below about 5.

Thus, in an embodiment, the present invention is further directed to a method of improving the deposition of conditioning and/or active agents on keratinous substrates, the method comprising:
(1) applying onto a keratinous substrate such as hair or skin, a cosmetic composition comprising:
  (a) from about 0.3 wt. %, based on the total weight of the composition, of at least one non-hydrophobically modified anionic polymer;
  (a) at least one cationic surfactant, including a cationizable surfactant;
  (b) at least one fatty alcohol;
  (c) at least one cosmetically acceptable solvent;
  (d) optionally, at least one silicone;
  (e) optionally, at least one nonionic surfactant; and (f) optionally, at least one fatty compound selected from non-silicone oils, esters, fatty acids, or a mixture thereof; and wherein the pH of the composition is below about 5.

In an embodiment, any one of the above-described methods further comprises a step of rinsing the keratinous substrate with water.

The cosmetic compositions described herein may be in any suitable physical form. Suitable forms include, but are not limited to low to moderate viscosity liquids, lotions, milks, gel creams, emulsion creams, pastes, clays, conditioners, masks, and the like. In an embodiment, the cosmetic compositions are rinse-off compositions.

The cosmetic compositions may be packaged in a variety of different containers, such as, for example, a ready-to-use container. Non-limiting examples of useful packaging include tubes, jars, caps, unit dose packages, and bottles, including squeezable tubes and bottles, pump bottles, and spray bottles.

Non-Hydrophobically Modified Anionic Polymer

The at least one non-hydrophobically modified anionic polymer of the present invention is not hydrophobically modified with a long alkyl chain. In an embodiment, when the at least one non-hydrophobically modified anionic polymer comprises an alkyl group, the alkyl group is less than 5 carbons.

In various embodiments, when the at least one non-hydrophobically modified anionic polymer comprises an alkyl group, the alkyl group is from 1 to 4 carbons or from 1 to 3 carbons or no more than 2 carbons.

In an embodiment, the at least one non-hydrophobically modified anionic polymer include copolymers of a (meth) acrylic acid and its esters, referred to herein as an (meth) acrylate copolymer. In some embodiments, the copolymer is an acrylates copolymer, which is used herein, refers to a copolymer of two or more monomers selected from the group consisting of acrylic acid, methacrylic acid, and their simple esters, e.g., lower alkyl esters such as methyl, ethyl esters propyl, butyl and pentyl esters. In some embodiments, the polymer refers to a copolymer of two or more monomers selected from the group consisting of acrylic acid, methacrylic acid and vinyl monomers, (meth)acrylamide. Such copolymers, which may be in the form of an aqueous dispersion, are commercially available from numerous sources, including ACUDYNE 180, ACUDYNE BOLD BH Dow Chemical, LUVIFLEX SOFT from BASF, LUVIMER 36D from BASF, DERMACRYL C from Akzo Nobel and SYNTRAN 5760 by Interpolymer. In some embodiments, the acrylates copolymer is an aqueous dispersion consisting of the ethyl ester of acrylic acid and the methyl ester of methacrylic acid, and which is commercially available from Daito Kasei under the tradename DAITOSOL 5000AD (CAS #2135-39-1, which is an aqueous emulsion having a solids content of about 50 percent.

In an embodiment, the at least one non-hydrophobically modified anionic polymer is a latex polymer, which is used herein, refers to an aqueous dispersion of a polymer.

In an embodiment, the at least one non-hydrophobically modified anionic polymer is not neutralized or partially neutralized.

In embodiment, the at least one non-hydrophobically modified anionic polymer is acrylates copolymer.

The total amount of the at least one non-hydrophobically modified anionic polymer may vary but is typically from about 0.3 to about 5 wt. %, or about 0.5 to about 4 wt. %, or about 0.6 to about 4 wt. %, or about 0.6 to about 3 wt. %, or about 0.7 to about 2.5 wt. %, or about 0.7 to about 2 wt %, or about 0.7 to about 1.5 wt. %, or about 0.7 to about 1.25 wt. %, or about 0.7 to about 1 wt. %, or about 0.7 to about 0.9 wt. %, based on the total weight of the cosmetic composition, including ranges and sub-ranges there between.

Thus, the least one non-hydrophobically modified anionic polymer is present, by weight, based on the total weight of the composition, in an amount from about 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 wt. %.

Cationic Surfactants Including Cationizable Surfactants

In accordance with the disclosure, compositions hereof may include at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactant comprises cetrimonium chloride, behentrimonium chloride, and mixtures thereof. Behentrimonium Chloride, also described by the technical names that include 1-Docosanaminium, N,N, N-Trimethyl-, Chloride, and N,N,N-Trimethyl-1-Docosanaminium Chloride, is the quaternary ammonium salt that conforms to the formula:

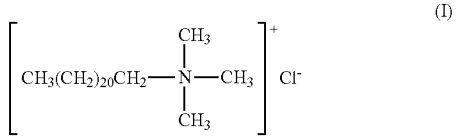

In accordance with some embodiments, the amount of each of the at least one cationic surfactant is from about 0.1 to about 5 wt. %, or about 0.1 to about 4 wt. %, or about 0.2 to about 4 wt. %, or about 0.3 to about 3 wt. %, or about 0.5 to about 3 wt. %, or any suitable combination, sub-combination, range, or sub-range thereof by weight, based on the weight of the composition. One of ordinary skill in the art, however, will appreciate that other ranges are within the scope of the invention. In some particular embodiments, the at least one cationic surfactant, including cationizable surfactants together with an acid neutralizer, is present from about 0.1 to about 5 wt. %, and an acid neutralizer is present from about 0.0.5 to about 1 wt. %, based on the weight of the composition.

Thus, any one of the at least one cationic surfactant is present, by weight, based on the total weight of the composition, from about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.2, 3.4, 3.5, 3.6, 3.8, 4, 4.2, 4.4, 4.5, 4.6, 4.8, 4.9, or 5 wt.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$ hydrocarbon-based chain.

A. Examples of quaternary ammonium salts that may especially be mentioned include: those corresponding to the general formula below:

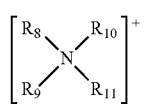

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyal, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula below:

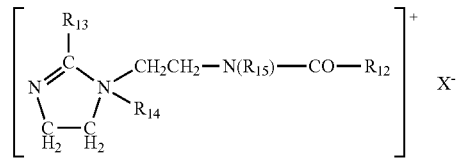

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$alkyl group, $R_{15}$ represents a hydrogen atom or a $C_1$-$C_4$alkyl group, $X^-$ is an anion chosen from the group of halides, phosphates, acetates, lactates, alkyl sulfates, alkyl- or alkylarylsulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo;

C. a quaternary diammonium or triammonium salt, in particular of formula:

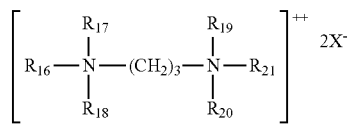

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, including cationizable surfactants together with an acid neutralizer, for example of the general structure R4-A-R5B wherein R4 is a saturated or unsaturated, straight or branched alkyl chain with 8 to 24 C atoms, R5 is a straight or branched alkyl chain with 1 to 4 C atoms, A is selected from:

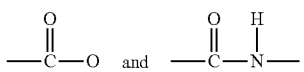

and B is selected from

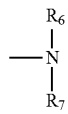

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

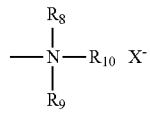

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24 C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines. in some embodiments, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethyl-amine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

Fatty Alcohol

In accordance with the disclosure, compositions hereof include at least one fatty alcohol.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture:lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by one or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

In accordance with the various embodiments, the amount of each of the at least one fatty alcohol is from about 0.5 to about 10 wt. %, or about 2 to about 9 wt. %, or about 3 to about 8 wt. %, or about 3.5 to about 7 wt. %, or about 4 to about 7 wt. %, or about 4.5 to about 6.5 wt. %, or about 5 to about 6 wt. %, or any suitable combination, sub-combination, range, or sub-range thereof by weight, based on the weight of the composition.

In certain preferred embodiments, the total amount of the at least one fatty alcohol is at least 3 wt. %, or at least 3.5 wt. %, or at least 4 wt. % or at least 4.5 wt. % or at least 5 wt. % or at least 5.5 wt. % or at least 6 wt. %, or is in an amount of from about 3 to about 10 wt. %, or about 3.5 to about 10 wt. %, or about 4 to about 9 wt. %, or about 4.5 to about 8.5 wt. %, or about 4.5 to about 8 wt. %, or about 5 to about 7.5 wt. %, or about 5.5 to about 7 wt. %, or about 5.5 to about 7 wt. %, or any suitable combination, sub-combination, range, or sub-range thereof by weight, based on the weight of the composition.

Thus, any one of the at least one fatty alcohol is present, by weight, based on the total weight of the composition, in an amount of from about 3, 3.5, 4, 4.5, 5, 5.5, 5.8, 6, 6.2, 6.5, 7, 7.5 or 8 wt. %.

Cosmetically Acceptable Solvent

The cosmetically acceptable solvent may be chosen from water, organic solvents, or mixtures thereof.

In an embodiment, the cosmetically acceptable solvent in the compositions of the present invention comprises water.

In an embodiment, the cosmetically acceptable solvent in the compositions of the present invention comprises at least one organic solvent.

In an embodiment, the cosmetically acceptable solvent in the compositions of the present invention comprises water and at least one organic solvent.

Water

The amount of water in the hair cosmetic compositions may be at least 50 wt. %, or from about 50 to about 95 wt. %, about 50 to about 90 wt. %, about 60 to about 90 wt. %, about 70 to about 88 wt. %, about 75 to about 86 wt. %, based on the weight of the composition, including ranges and sub-ranges there between.

Organic Solvents

Non-limiting examples of organic solvents include, for example, alcohols (for example, $C_{1-15}$, $C_{2-10}$, or $C_{1-6}$ alcohols), organic solvents, polyols (polyhydric alcohols and glycols (e.g., glycerin, propylene glycol, butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycerin or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In certain embodiments, the at least one organic solvent (non-silicone solvents) includes one or more of propylene glycol, glycerin, ethanol, isopropanol, caprylyl glycol, and benzyl alcohol.

The total amount organic solvent(s) in the hair cosmetic composition, if present, can vary but is typically about 0.01 to about 10 wt. %, based on the total weight of the hair cosmetic composition. In some cases, the total amount of water-soluble solvent(s) is about 0.05 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %, including all ranges and subranges there between, based on the total weight of the hair cosmetic composition.

In an embodiment, the cosmetically acceptable solvent in the compositions of the present invention comprises water and an organic solvent selected from glycerin, propylene glycol, butylene glycol, caprylyl glycol, isopropyl alcohol, denatured alcohol or ethanol or a mixture thereof.

In an embodiment, the at least one organic solvent is in an amount of from about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 0.5 to about 4 wt. %, or about 0.5 to about 3 wt. %, including all ranges and subranges there between, based on the total weight of the cosmetic composition.

Amino Functionalized Silicones

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

In some instances, the amino-functionalized silicones are selected from compounds of the following formula:

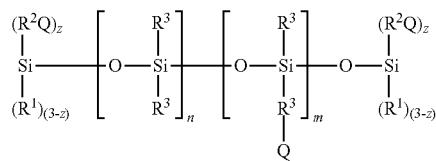

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms); p each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4{}_2$ and $-NR^4(CH_2)_xNR^4{}_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

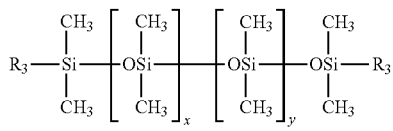

wherein $R_3$ is hydroxyl or $OR_5$, $R_5$ is a $C_1$ to $C_4$ alkyl group, $R_4$ is a group with a structure according to the following formula:

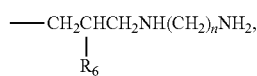

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions XIAMETER 2-8299 (Dow Corning/Dow Chemical), BELSIL ADM 4000 E (Wacker), DC2-1766, DC2-1784, and microemulsions DC2-1865 and DC2-1870 from Dow Corning, or cross-linked silicone gums, such as DC X2-1787 or DC X2-1391 from Dow Corning.

In an embodiment, the amino functionalized silicone of the compositions of the present invention includes amodimethicone. The amodimethicone may be commercially available as an emulsion comprising amodimethicone, trideceth-6, and cetrimonium chloride under the tradenames XIAMETER 2-8299 or DOWSIL 2-8299 (Dow Corning/Dow Chemical). The amodimethicone may also be available as an emulsion under the tradename, BELSIL ADM 4000 E (Wacker).

In accordance with the various embodiments, the amount of the at least one amino functionalized silicone is from about 0.1 to about 3 wt. %, or preferably about 0.3 to about 2.5 wt. %, or more preferably, about 0.4 to about 2 wt. %, or more preferably, about 0.5 to about 1.5 wt. %, or any suitable combination, sub-combination, range, or sub-range thereof by weight, based on the weight of the composition. One of ordinary skill in the art, however, will appreciate that other ranges are within the scope of the invention.

Thus, any one of the at least one amino functionalized silicone is present, by weight, based on the total weight of the composition, in an amount of from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Fatty Compounds

The at least one fatty compounds of the compositions of the present invention may be selected from plant-based oils, plant-based butters, plant-based triglycerides, or mixtures thereof.

Non-limiting examples of plant-based or vegetal oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander oil, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil, sunflower oil, olive oil, marula oil, corn oil, argan oil, soybean oil, marrow oil, flax oil, sesame oil, hazelnut oil, apricot oil, arara oil, shea butter oil and rapeseed oil.

Suitable fatty compounds for use in the compositions of the present invention can also be selected from plant-based or vegetal butters such as shea butter (*Butyrospermum parkii*), Karite Nilotica butter (*Butyrospermum parkii*), galam butter, (*Butyrospermum parkii*), Borneo butter or fat or tengkawang tallow (*Shorea stenoptera*), shorea butter, illipe butter, madhuca butter or *Bassia madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya butter (*Kpangnan*) (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter.

In a preferred embodiment, the suitable fatty compound of the present invention is selected from shea butter (*Butyrospermum parkii*), *Cocos nucifera* (coconut) oil (or coconut oil), or a mixture thereof, preferably, coconut oil The total amount of the fatty compounds in the composition may vary but is typically from of about 0.1 to about 10 wt %, about 0.1 to about 9 wt. %, or about 0.2 to about 8 wt. %, or about 0.3 to about 7 wt. %, or about 0.4 to about 7 wt. %, or about 0.4 to about 6.5 wt. %, or about 0.5 to about 6 wt. %, or 0.5 to about 5 wt. %, or about 0.1 to about 5 wt. %, or about 0.5 to about 4.5 wt. %, or about 0.8 to about 4.2 wt. %, or about 1 to about 4 wt. %, or about 1.2 to about 4 wt. %, or about 1.2 to about 3.5 wt. %, or about 1.5 to about 3 wt. %, r about 1 to about 3 wt. %, or about 1.5 to about 2.5 wt. %, based on the total weight of the composition, including ranges and sub-ranges there between.

Thus, the fatty compounds is present, by weight, based on the total weight of the composition, in an amount from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5 to about 5 wt. %, including increments and ranges therein and there between.

Esters

The esters may be selected from fatty esters, cetyl esters, isopropyl esters, glyceryl (glycerol) esters, dialkyl esters, diesters with octanoic acid and propylene glycol (for example, mixture of the propylene glycol diesters of caprylic and capric acids, INCI: propylene glycol dicaprylate/dicaprate), or mixtures thereof.

Thus, the total amount of esters in the composition, may vary but is typically from about 0.01 to about 6 wt %, such as about 0.05 to about 5.5 wt. %, or about 0.05 to about 5 wt. %, or about 0.05 to about 4.5 wt. %, or about 0.1 to about 4 wt. %, or about 0.2 to about 3.5 wt. %, or about 0.3 to about 3 wt. %, or about 4 to about 2.5 wt. %, or about 0.5 to about 2 wt. %, or about 0.5 to about 1.5 wt. %, based on the total weight of the composition, including ranges and sub-ranges there between.

Additional Ingredients

The compositions of the present invention may further comprise additional/optional ingredients such as nonionic surfactants.

The nonionic surfactants may be selected from alkoxylated fatty alcohols such as oleth-3, oleth-10, oleth-20, trideceth-5, trideceth-6, trideceth-10, PPG-1 trideceth-6, laureth-12, steareth-20, and combinations thereof, Other Components In one or more embodiments, the hair cosmetic compositions described herein may contain one or more additional ingredients (additives and miscellaneous ingredients). Examples include, but are not limited to amphoteric surfactants, anionic surfactants, emulsifiers (such as sorbitan esters or polysorbates), thickeners (such as polysaccharide-based thickeners other than cationic guar gums), film formers, other polymers such as cationic polymers, amphoteric polymers, polyquaternium compounds such as polyquaternium-4, polyquaternium-6, polyquaternium-7, polyquaternium-10, polyquaternium-11, polyquaternium-22, polyquaternium-37, polyquaternium-53, polyquaternium-67, etc.), proteins, hydrolyzed proteins, amino acids, fragrance, pH adjusters, chelants, and preservatives.

In an embodiment, the compositions of the present disclosure are in the form of a leave-on product such as a caring product for curly hair (such as combing creams), anti-frizz hair product, or rinse-off or leave-on mask or treatment product.

In an embodiment, the compositions of the present disclosure are in the form of a rinse-off product such as a conditioner product or a mask product or a shampoo-conditioner product (2 in 1).

In an embodiment, the compositions of the present disclosure are in the form of a leave-on product such as a hair or skin treatment product.

In an embodiment, the compositions of the present disclosure are in the form of a leave-on or a rinse-off conditioner.

In an embodiment, the compositions of the present disclosure are in the form of a cream.

In an embodiment, the compositions of the present disclosure are in the form of an emulsion such as an oil-in-water emulsion or a water-in-oil emulsion. In an embodiment, the emulsion is in the form of a cream or a lotion.

pH and Viscosity

The cosmetic composition of the present disclosure has a pH a ranging from about 2.5 to about 4.8 or from about 2.7 to about 4.5 or from about 3 to about 4.5, including ranges and sub-ranges there between.

In various embodiments, the cosmetic composition of the present disclosure has pH of about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, or 4.9.

In an embodiment, the cosmetic composition of the present disclosure has an initial viscosity (after preparation of the composition) of equal to or greater than 10 Pa·s, or from about 10 to about 100 Pa·s, or about 5 to about 100 Pa·s, or about 5 to about 50 Pa·s, including ranges and sub-ranges there between, at a shear rate above 1 (1/s) and below $10^1$ 1/s as measured a rheometer (DHR-2, TA instruments, New Castle, DE, USA).

In an embodiment, the cosmetic composition of the present disclosure has an initial viscosity (after preparation of the composition) of equal to or less than 10 Pa·s, or from about 1 to about 10 Pa·s, or about 2 to about 10 Pa·s, or about 5 to about 50 Pa·s, including ranges and sub-ranges there between, at a shear rate above $10^1$ 1/s and below $10^2$ 1/s as measured a rheometer (DHR-2, TA instruments, New Castle, DE, USA).

In an embodiment, when the pH of the composition is increased to above 5, the viscosity of the composition drops to a viscosity below 1 Pa·s, such as from below 1 to about 0.1 Pa·s, at a shear rate above $10^1$ (1/s) and below $10^2$ 1/s as measured a rheometer (DHR-2, TA instruments, New Castle, DE, USA).

In an embodiment, when the composition is diluted at least 3 times, the viscosity of the composition drops to a viscosity below 1 Pa·s, such as from below 1 to about 0.1 Pa·s, at a shear rate above $10^1$ (1/s) and below $10^2$ 1/s as measured a rheometer (DHR-2, TA instruments, New Castle, DE, USA).

Methods

Another aspect of the invention pertains to methods of using the cosmetic compositions described herein. In particular, when the cosmetic compositions are to be applied to hair, i.e., they are hair cosmetic compositions, and the methods generally comprise applying any of the hair cosmetic compositions described to hair. The hair cosmetic compositions may be useful in a variety of settings, and either for chemically treated or pre-alkalized hair or untreated hair. Pre-alkalized hair can include chemically relaxed/straightened hair or chemically dyed (with oxidative dyes) or bleached or lightened/highlighted hair, i.e., hair treated with products that result in raising the pH of the hair to an alkaline pH. Use of the compositions of the present invention on hair may include as part of a shampoo, part of a conditioner or as a conditioner, as a pre-treatment, or after cleansing or conditioning or washing the hair, or a treatment for caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

The hair cosmetic composition may be allowed to remain on the hair for a period of time, for example from about a few seconds (1, 3, 5, or 10 seconds) to about 10, 20, or 30 minutes, or longer such as up to about one hour or up to about two hours or up to about three hours or up to about four hours or up to about five hours or up to about six hours or up to about seven hours or up to about eight hours or up to about 12 hours or overnight.

The hair cosmetic compositions may be useful for treating chemically treated hair.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

Kits

The cosmetic compositions of the instant disclosure may be incorporated into a kit. For example, the kits may include at least one cosmetic composition according to the instant disclosure. The kits may also include one or more hair cosmetic compositions (according the instant disclosure), such as a shampoo and/or a conditioner and/or a mask and/or other hair treatment or styling product.

Implementation of the present disclosure is provided by way of the following examples. The examples serve to illustrate the technology without being limiting in nature.

Example I: Compositions

TABLE 1

Formulation Examples

| INGREDIENT TYPE | INGREDIENT INCI NAME | EX. A (invention) | EX. B (comparative) |
|---|---|---|---|
| CATIONIC SURFACTANT | BEHENTRIMONIUM CHLORIDE | 2.1 | 2.1 |
| CATIONIC SURFACTANT | CETRIMONIUM CHLORIDE | 0.02 | 0.02 |
| ANIONIC POLYMER | ACRYLATES COPOLYMER(1) | 0.8 | — |
| SILICONE | AMODIMETHICONE | 1.4 | 1.4 |
| FATTY ALCOHOL | CETEARYL ALCOHOL | 5.8 | 5.8 |
|  | TRIDECETH-6 | 0.1 | 0.1 |
| NONIONIC SURFACTANT | POLYSORBATE 80 | 0.1 | — |
| FATTY COMPOUND | ONE OR MORE OF PLANT-BASED OIL OR BUTTER, HYDROCARBON OILS, ESTERS | </=10 | </=10 |
| ORGANIC SOLVENTS | ONE OR MORE OF GLYCERIN, PROPYLENE GLYCOL, BUTYLENE GLYCOL, CAPRYLYL GLYCOL, ISOPROPYL ALCOHOL, DENAT. ALCOHOL | </=10 | </=10 |
| ADDITIVES OR MISCELLANEOUS INGREDIENTS | ONE OR MORE OF PRESERVATIVES, pH ADJUSTERS, CHELANTS, COLORANTS, SALT, FRAGRANCE, VITAMINS, PLANT EXTRACTS, PROTEINS/AMINO ACIDS/PROTEIN HYDROLYSATES | <=1.0 | <=1.0 |
|  | WATER | QS 100 | QS 100 |

(1)Commercially availabe under the tradename of LUVIFLEX SOFT from the company BASF Process of Making the Invention Compositions The invention example A was prepared according to the following general process:
The formulation was prepared by:
heating water to about 70° C.,
then adding the cetearyl alcohol, amodimethicone and behentrimonium chloride until completely dispersed, cooling to about 50° C.,
adding acrylates copolymer, other optional additives (preservatives, organic solvent, surfactants, perfume and dyes etc.),
then continuing to cool down to room temperature.

The pH of the inventive formulas made according to the procedure above ranged from about 2.5 to less than 5. The resulting inventive formulas were also stable after 2 months at 45° C. and 4° C., respectively, i.e., there was no phase separation or precipitation, even with the combination of a cationic compound (cationic surfactant) and an anionic compound (acrylates copolymer) in the formulas.

Example II Viscosity, pH, and Dilution Studies

The following table shows the changes in properties of the inventive formulations such as texture and viscosities when their pH was changed or when the formulations were diluted with water. The viscosities of the formulations were measured using a rheometer (DHR-2, TA instruments, New Castle, DE, USA) and 40 mm parallel plate geometry. The 1 mm gap between the parallel plates was chosen. All tests were conducted at 25° C. and atmospheric pressure. The sample was subjected to shear ramp starting from 0.1 1/s to 1000 1/s within a 300 second period. The time interval between data points is 1 s. The shear stress response was recorded for every data point.

The pH of the formulations was changed or adjusted by adding sodium hydroxide solution or other appropriate pH modifiers.

The textures of the formulations were evaluated using a polarized microscope.

TABLE 2

|  | EX. A (invention) | EX. B (comparative) |
|---|---|---|
| pH of composition (non-diluted) | 4.2 | 4.4 |
| Range of viscosity (Pa · s) over a shear rate of 10 to 1 × 10³ 1/s | 7.0-0.26 (FIG. 1A) | 2.2-0.049 (FIG. 1B) |
| Texture of composition | Lamellar structure and creamy | Lamellar structure and creamy |

TABLE 2-continued

|  | EX. A (invention) | EX. B (comparative) |
|---|---|---|
| pH change | | |
| Change in the pH of the composition | Increased to 5.6 | Increased to 5.5 |
| Viscosity and texture of composition after change in pH | viscosity significantly decreased and composition structure broke down; phase separation/precipitation | change in viscosity was very small |
| Range of viscosity (Pa · s) over a shear rate of 10 to 1 × 10$^3$ 1/s after change in pH | 0.8-0.028 (FIG. 1A) | 1.03-0.040 (FIG. 1B) |
| 3X dilution of Ex. A or Ex. B formulas with water (extraneous*) | | |
| pH of the composition after 3x dilution | 4 | 4.7 |
| Viscosity and texture of composition after 3x dilution | viscosity significantly decreased significantly and composition structure broke down | change in viscosity was very small |
| Range of viscosity (Pa · s) over a shear rate of 10 to 1 × 10$^3$ 1/s after 3x dilution | 1.94-0.052 (FIG. 2A) | 1.88-0.063 (FIG. 2B) |

*extraneous water refers to water that is not part of the formulation when it is first prepared The data in Table 3 can be visualized in FIGS. 1 to 2. In FIG. 1A, it can be seen that the viscosity of the inventive composition, Ex. A, significantly decreased over a shear rate of 10 to 1×10$^3$ 1/s when the pH of the inventive composition Ex. A was increased to over 5, i.e., to about 5.6. Thus, while the inventive composition initially has a higher viscosity or is thicker which prevents or reduces dripping of the composition while it is being delivered to a substrate such as hair, a change in pH of the composition resulting in a significant decrease in viscosity allows for easier spreadability and application on the surface such as hair fibers which results in better and homogeneous deposition of active agents and/or conditioning agents and/or styling agents on the surface. At the same time, the decrease in viscosity makes it easier and faster to rinse or remove the composition from the hair with water (fast wash or fast rinse effect or improved rinsability). The cleansing or rinsing process would therefore require less water.

Thus, when the inventive composition is exposed to an alkaline or basic environment such as when mixed with an alkaline composition or when applied on chemically treated hair (or pre-alkalized hair) which has previously been treated with hair dyes or relaxer products that are typically alkaline and which typically have residual alkalinity, the pH of the inventive composition can increase, thereby resulting in a significant decrease in the viscosity which facilitates the spreadability, ease of application, and more homogeneous application of the composition on a substrate. The significant decrease in viscosity due to an increase of the pH of the composition is associated with the unique and improved rinsability or removability or fast wash/rinse property of the compositions of the instant disclosure (requiring less water during rinsing).

In contrast, a very small or insignificant viscosity change was observed for the comparative composition, Ex. B, even when its pH was increased to over 5, i.e., to about 5.5 (FIG. 1B). This insignificant viscosity change was evident over a shear rate ranging from 10 to 1×10$^3$ 1/s; such a result indicates that the spreadability and application attributes of the composition on a substrate and/or in the rinsability property of the composition from a substrate would not be significantly impacted.

As for diluting the inventive composition with water, such as by a 3× dilution with water, its viscosity significantly decreases from the initial viscosity of the composition (FIG. 2A). The decrease in viscosity allows for easier spreadability and application of the composition on a surface such as the surface of hair fibers which results in better and homogeneous deposition of active agents and/or conditioning agents on the surface. The viscosity drop also allows for easier and faster removal of the composition from the surface (fast wash or fast rinse effect or improved rinsability). The cleansing or rinsing process would therefore require less water. Thus, decrease in viscosity due to dilution, which mimics the application onto wet hair and/or the addition of extraneous water, is associated with the unique and improved rinsability or removability or fast wash/rinse property of the compositions of the instant disclosure (requiring less water during rinsing).

In contrast, the comparative composition Ex. B, exhibited only a very slight change in viscosity upon dilution with water over a shear rate ranging from 10 to 1×10$^3$ 1/s (FIG. 2B); such a result indicates that the spreadability and application attributes of the composition on a substrate and/or in the rinsability property of the composition from a substrate would not be significantly impacted.

As a conclusion, the inventive composition was found to be responsive to a change in pH and/or dilution with water that results in a significant decrease in viscosity. This viscosity change can result from either applying the composition on pre-alkalized hair or by diluting it with water (such as in hair cleansing or conditioning activities). The resulting decrease in viscosity impacts the spreadability and application of the composition on a surface such as hair. When the viscosity decreases, the composition becomes easier to spread and apply on the surface and to be removed or rinsed/washed off from the hair.

Example III Hair Swatch Studies

The inventive composition Ex. A and comparative composition Ex. B were each applied onto wet hair swatches of medium degree of curliness. The swatches were pre-shampooed, rinsed with water, treated with either the inventive composition or the comparative composition, and then rinsed with water.

In one study, wet swatches were placed in a humidity chamber (80% RH) at 25 degrees centigrade for 2 days. FIG. 3A (left image) shows the visual appearance of the swatches before placing them in the humidity chamber. The swatch on the left was treated with Ex. A inventive composition and the swatch on the right was treated with Ex. B comparative composition (initial). FIG. 3B (right image) shows the visual appearance of the swatches after 2 days in the humidity chamber (after 2 days). It is evident from the images that at the initial stage, the swatch treated with the inventive composition was less frizzy, had better curl definition and shape and had a sleeker look as compared to the swatch treated with the comparative composition. The inventive and comparative composition imparted a comparable conditioning effect to the hair. It was also evident that after 2 days in high humidity, even if the swatch treated with the inventive composition was more volumized compared to initial stage, it was significantly less frizzy, had significantly better curl definition and shape and significantly less volume as compared to the swatch treated with the comparative composition.

In another study, wet swatches were allowed to air dry at 25 degrees centigrade for 2 days. FIG. 4A (left image) shows the visual appearance of the swatches before air drying them. The swatch on the left was treated with Ex. B comparative composition and the swatch on the right was treated with Ex. A inventive composition (initial). FIG. 4B (right image) shows the visual appearance of the swatches after 2 days of air drying (after 2 days). From the images at the initial stage, the swatches had comparable appearances—very small amount of frizz, curl definition and shape and sleek and conditioned look as compared to the swatch treated with the comparative composition. However, after 2 days of air drying, even if the swatch treated with the inventive composition was more volumized compared to initial stage, it was significantly less frizzy, had significantly better curl definition and shape and had significantly less volume as compared to the swatch treated with the comparative composition.

Overall, the inventive composition imparted significantly better anti-frizz, curl definition, and sleek look or less volumized look to natural curly hair compared to the comparative composition which does not contain the anionic copolymer.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counterion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

As used herein, the term "cosmetic composition" is understood to include "personal care" compositions.

Some of the various categories of components identified for the compositions of the present disclosure may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.3 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
    (a) at least 0.3 wt. % of at least one non-hydrophobically modified anionic copolymer of two or more monomers selected from acrylic acid, methacrylic acid, or simple esters thereof, wherein the simple esters thereof are selected from methyl, ethyl, propyl, butyl, or pentyl esters;
    (b) from about 0.1 to about 5 wt. % of at least one cationic surfactant;
    (c) from about 2 to about 9 wt. % of at least one fatty alcohol;
    (d) from about 60 to about 90 wt. % of water;
    (e) optionally, at least one silicone;
    (f) at least one nonionic surfactant; and
    (g) at least one fatty compound selected from plant-based oils, hydrocarbon oils, esters, fatty acids, or a mixture thereof; and
    wherein the pH of the cosmetic composition is below 5; the cosmetic composition is an emulsion;
    the composition has a lamellar structure that breaks down and viscosity of the cosmetic composition decreases if the pH of the cosmetic composition is raised to 5.6; and
    all percentages by weight are based on a total weight of the cosmetic composition.

2. The cosmetic composition of claim 1, wherein the at least one non-hydrophobically modified anionic copolymer is not neutralized or partially neutralized.

3. The cosmetic composition of claim 1, wherein the at least one non-hydrophobically modified anionic copolymer is an aqueous dispersion.

4. The cosmetic composition of claim 1, wherein the at least one non-hydrophobically modified anionic copolymer is in an amount of from about 0.5 wt. % to about 5 wt. %, based on the total weight of the cosmetic composition.

5. The cosmetic composition of claim 1, wherein the at least one cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, or mixtures thereof.

6. The cosmetic composition of claim 1, wherein the at least one cationic surfactant is in an amount of from about 0.1 to about 5 wt. %, based on the total weight of the cosmetic composition.

7. The cosmetic composition of claim 1, wherein the at least one fatty alcohol is selected from cetyl alcohol, stearyl alcohol, cetearyl alcohol, behenyl alcohol, lauryl alcohol, myristic or myristyl alcohol, arachidyl alcohol, lignoceryl alcohol, ceryl alcohol, montanyl alcohol, myricylic alcohol, decyl alcohol, undecyl alcohol, or a mixture thereof.

8. The cosmetic composition of claim 1, wherein the pH of the composition is from about 2.5 to about 4.8.

9. The cosmetic composition of claim 1 comprising the at least one silicone of (e), wherein the at least one silicone is selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, or mixtures thereof.

10. The cosmetic composition of claim 9, wherein the at least one silicone is in an amount of from about 0.1 to about 5 wt. %, based on the total weight of the cosmetic composition.

11. The cosmetic composition of claim 1, wherein the at least one nonionic surfactant is selected from alkoxylated fatty alcohols, sorbitan derivatives, polyethylene glycol ester of fatty acids or alkoxylated carboxylic acids, or a mixture thereof.

12. The cosmetic composition of claim 11, wherein the at least one nonionic surfactant is in an amount of from about 0.05 to about 10 wt. %, based on the total weight of the cosmetic composition.

13. The cosmetic composition of claim 1, wherein the at least one fatty compound is in an amount of from about 0.1 to about 10 wt. %, based on the total weight of the cosmetic composition.

14. A cosmetic composition comprising:
   (a) from about 0.5 to about 4 wt. % of an acrylates copolymer;
   (b) from about 0.2 to about 4 wt. % of at least one cationic surfactant selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, or a mixture thereof;
   (c) from about 2 to about 7 wt. % of at least one fatty alcohol selected from cetyl alcohol, stearyl alcohol, cetearyl alcohol, behenyl alcohol, lauryl alcohol; myristic or myristyl alcohol, arachidyl alcohol, lignoceryl alcohol;
   ceryl alcohol, montanyl alcohol, myricylic alcohol, decyl alcohol, undecyl alcohol, or a mixture thereof;
   (d) from about 60 to about 90 wt. % of water:
   (e) optionally, from about 0.1 to about 2 wt. % of at least one silicone;
   (f) from about 0.05 to about 2 wt. % of at least one nonionic surfactant; and
   (g) from about 0.1 to about 5 wt. % of at least one fatty compound selected from plant-based oils, hydrocarbon oils, esters, fatty acids, or a mixture thereof; and
      wherein the pH of the composition is from about 2.5 to about 4.8,
      the cosmetic composition is an emulsion,
      the composition has a lamellar structure that breaks down and viscosity of the cosmetic composition decreases if the pH of the cosmetic composition is raised to 5.6,
      the cosmetic composition is essentially free from anionic surfactants, and
      all weights being based on a total weight of the cosmetic composition.

15. A method of treating hair, the method comprising applying onto hair, the cosmetic composition of claim 1.

16. A method of treating a keratinous substrate selected from hair or skin, the method comprising applying onto the keratinous substrate, a cosmetic composition of claim 1.

17. The method of claim 16, wherein the keratinous substrate is hair, and the hair has been pre-alkalized or previously contacted with an alkaline treatment.

18. The method of claim 16, wherein the method further comprises rinsing the keratinous substrate with water following application of the cosmetic composition onto the keratinous substrate.

19. The method of claim 16, wherein the method imparts a fast wash or a fast rinse effect to the rinsing step.

20. A cosmetic composition consisting of:
   (a) from about 0.5 to about 4 wt. % of acrylates copolymer;
   (b) from about 0.2 to about 4 wt. % of at least one cationic surfactant;
   (c) from about 2 to about 7 wt. % of at least one fatty alcohol selected from cetyl alcohol, stearyl alcohol, cetearyl alcohol, behenyl alcohol, lauryl alcohol; myristic or myristyl alcohol, arachidyl alcohol, lignoceryl alcohol; ceryl alcohol, montanyl alcohol, myricylic alcohol, decyl alcohol, undecyl alcohol, or a mixture thereof;
   (d) from about 60 to about 90 wt. % of water:
   (e) optionally, from about 0.1 to about 2 wt. % of at least one silicone;
   (f) from about 0.05 to about 2 wt. % of at least one nonionic surfactant;
   (g) from about 0.1 to about 5 wt. % of at least one fatty compound selected from plant-based oils, hydrocarbon oils, esters, fatty acids, or a mixture thereof;
   (h) one or more preservatives, pH adjusters, chelants, colorants, salts, fragrances, vitamins, plant extracts, proteins, protein hydrolysates, amino acids, or a combination thereof;
      wherein the pH of the cosmetic composition is from about 2.5 to about 4.8, the cosmetic composition is an emulsion, and all weights being based on a total weight of the cosmetic composition.

* * * * *